United States Patent
Mathur et al.

(10) Patent No.: US 6,610,528 B1
(45) Date of Patent: *Aug. 26, 2003

(54) MICROBIAL ENRICHMENT USING A CONTAINER HAVING A PLURALITY OF SOLID SUPPORT PARTICLES

(75) Inventors: Eric J. Mathur, Carlsbad, CA (US); Jeffrey L. Stein, San Diego, CA (US); Martin Keller, San Diego, CA (US); Karl Rusterholz, Clackamas, OR (US)

(73) Assignee: Diversa Corporation, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/918,793

(22) Filed: Aug. 26, 1997

(51) Int. Cl.$^7$ .............................. C12M 1/00; C12N 1/00; C12N 1/02; C12N 11/00
(52) U.S. Cl. .................. 435/243; 435/174; 435/177; 435/261; 435/283.1; 435/308.1
(58) Field of Search ................................. 435/261, 287, 435/288, 262.5, 174, 177, 243, 283.1, 308.1, 262, 287.9, 288.1; 210/600, 602, 610

(56) References Cited

U.S. PATENT DOCUMENTS

| | | | | |
|---|---|---|---|---|
| 4,920,063 A | * | 4/1990 | Ward, Jr. ........................ | 435/7 |
| 4,941,615 A | * | 7/1990 | Bolduc ........................ | 239/309 |
| 5,132,229 A | * | 7/1992 | Ward, Jr. ..................... | 435/288 |
| 5,510,242 A | * | 4/1996 | Blais et al. ................. | 435/7.32 |

* cited by examiner

Primary Examiner—David M. Naff
Assistant Examiner—Debunch K. Ware
(74) Attorney, Agent, or Firm—Gray Cary Ware & Freidenrich, LLP; Lisa A Haile

(57) ABSTRACT

A method and device for collection and concentration of microbes via selectively attracting microbes to specific substrates chemically conjugated to a solid surface, such as a particle, are provided. Further, a method for selectively enriching for specific microorganisms using a device for collecting populations of microorganisms from an environmental sample comprising a solid support having a surface for attachment of an enrichment media is provided. The method for selectively enriching one or more populations of microorganisms from an in situ environment includes providing a device which has a container having a plurality of solid support particles in the container and a selective microbial enrichment media chemically attached thereto the particles. The container also has permeable openings for the microorganisms to provide entry of them therein so that the microbes will contact the enrichment media. The microorganisms are collected and concentrated in the device by placing it into the environment and the microorganisms are attracted to it and thereby migrate into the device through the permeable openings. The populations of microorganisms may be enriched in the device with a microbial attractant and growth inhibitor in the media and removed therefrom the device. The microorganisms enriched in the device include extremophiles. The solid support particles include glass, silica aerogel or a combination thereof. Glass beads may also be used as the solid support particles.

16 Claims, 2 Drawing Sheets

MICROBIAL ENRICHMENT USING A CONTAINER HAVING A PLURALITY OF SOLID SUPPORT PARTICLES

FIELD OF THE INVENTION

The present invention relates to methods for capturing samples for evaluation. More particularly, the present invention relates to an approach which allows the collection and concentration of microbes, possessing genes encoding specific enzymes or small molecule pathways, from complex or dilute microbial populations in aqueous or terrestrial environments.

BACKGROUND OF THE INVENTION

There is a critical need in the chemical industry for efficient catalysts for the practical synthesis of optically pure materials; enzymes can provide the optimal solution. All classes of molecules and compounds that are utilized in both established and emerging chemical, pharmaceutical, textile, food and feed, detergent markets must meet stringent economical and environmental standards. The synthesis of polymers, pharmaceuticals, natural products and agrochemicals is often hampered by expensive processes which produce harmful byproducts and which suffer from low enantioselectivity. Enzymes have a number of remarkable advantages which can overcome these problems in catalysis: they act on single functional groups, they distinguish between similar functional groups on a single molecule, and they distinguish between enantiomers. Moreover, they are biodegradable and function at very low mole fractions in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, selectivity, the ability to carry out multi-step transformations in a single reaction vessel, along with the concomitant reduction in environmental burden, has led to the increased demand for enzymes in chemical and pharmaceutical industries. Enzyme-based processes have been gradually replacing many conventional chemical-based methods. A current limitation to more widespread industrial use is primarily due to the relatively small number of commercially available enzymes. Only ~300 enzymes (excluding DNA modifying enzymes) are at present commercially available from the >3000 non DNA-modifying enzyme activities thus far described.

The use of enzymes for technological applications also may require performance under demanding industrial conditions. This includes activities in environments or on substrates for which the currently known arsenal of enzymes was not evolutionarily selected. Enzymes have evolved by selective pressure to perform very specific biological functions within the milieu of a living organism, under conditions of mild temperature, pH and salt concentration. For the most part, the non-DNA modifying enzyme activities thus far described have been isolated from mesophilic organisms, which represent a very small fraction of the available phylogenetic diversity. The dynamic field of biocatalysis takes on a new dimension with the help of enzymes isolated from microorganisms that thrive in extreme environments. Such enzymes must function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. Enzymes obtained from these extremophilic organisms open a new field in biocatalysis.

For example, several esterases and lipases cloned and expressed from extremophilic organisms are remarkably robust, showing high activity throughout a wide range of temperatures and pHs. The fingerprints of five of these esterases show a diverse substrate spectrum, in addition to differences in the optimum reaction temperature. As seen in FIG. 1, esterase 5 (EST5) recognizes only short chain substrates while esterase 2 (EST2) only acts on long chain substrates in addition to a significant difference in the optimal reaction temperature. These results suggest that more diverse enzymes fulfilling the need for new biocatalysts can be found by screening biodiversity.

Furthermore, virtually all of the enzymes known so far have come from cultured organisms, mostly bacteria and more recently archaea. Traditional enzyme discovery programs rely solely on cultured microorganisms for their screening programs and are thus only accessing a small fraction of natural diversity. Several recent studies have estimated that only a small percentage, conservatively less than 1%, of organisms present in the natural environment have been cultured (see Table I). Amann et al., *Microbiol. Rev.* 59:143 (1995); Barnes et al., *Proc. Natl. Acad. Sci.* 91:1609 (1994); Torvisk et al., *Appl. Environm. Microbiol.* 56:782 (1990). Hence, this vast majority of microorganisms represents an untapped resource for the discovery of novel biocatalysts.

Within the last decade there has also been a dramatic increase in the need for bioactive compounds with novel activities. This demand has arisen largely from changes in worldwide demographics coupled with the clear and increasing trend in the number of pathogenic organisms that are resistant to currently available antibiotics. For example, while there has been a surge in demand for antibacterial drugs in emerging nations with young populations, countries with aging populations, such as the US, require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the US alone. As a response to this trend pharmaceutical companies have significantly increased their screening of microbial diversity for compounds with unique activities or specificities.

There are several common sources of lead compounds (drug candidates), including natural product collections, synthetic chemical collections, and synthetic combinatorial chemical libraries, such as nucleotides, peptides, or other polymeric molecules. Each of these sources has advantages and disadvantages. The success of programs to screen these candidates depends largely on the number of compounds entering the programs, and pharmaceutical companies have to date screened hundred of thousands of synthetic and natural compounds in search of lead compounds. Unfortunately, the ratio of novel to previously-discovered compounds has diminished with time. The discovery rate of novel lead compounds has not kept pace with demand despite the best efforts of pharmaceutical companies. There exists a strong need for accessing new sources of potential drug candidates.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism hence their name—"secondary metabolites". Secondary metabolites that influence the growth or survival of other organisms are known as "bioactive" compounds and serve as key components of the chemical defense arsenal of both micro- and macroorganisms. Humans have exploited these compounds for use as antibiotics, antiinfectives and other bioactive compounds with activity against a broad range of prokaryotic and eukaryotic pathogens. Approximately 6,000 bioactive compounds of microbial origin have been characterized, with more than 60% produced by the gram positive soil bacteria of the genus Streptomyces. Of these, at least 70 are currently used for biomedical and agricultural applications. The largest class of bioactive compounds, the polyketides, include a broad range of antibiotics, immunosuppressants and anticancer agents which together account for sales of over $5 billion per year.

Despite the seemingly large number of available bioactive compounds, it is clear that one of the greatest challenges facing modern biomedical science is the proliferation of antibiotic resistant pathogens. Because of their short generation time and ability to readily exchange genetic information, pathogenic microbes have rapidly evolved and disseminated resistance mechanisms against virtually all classes of antibiotic compounds. For example, there are virulent strains of the human pathogens Staphylococcus and Streptococcus that can now be treated with but a single antibiotic, vancomycin, and resistance to this compound will require only the transfer of a single gene, vanA, from resistant Enterococcus species for this to occur. When this crucial need for novel antibacterial compounds is superimposed on the growing demand for enzyme inhibitors, immunosuppressants and anti-cancer agents it becomes readily apparent why pharmaceutical companies have stepped up their screening of microbial diversity for bioactive compounds with novel properties. There is still tremendous biodiversity that remains untapped as the source of lead compounds.

The present invention provides a path to access biodiversity for a variety of purposes, including the use in the eventual discovery of novel bioactivities.

SUMMARY OF THE INVENTION

The present invention provides a means for selectively attracting microbes to specific substrates chemically conjugated to a solid surface. The invention further provides for the enrichment of these microbes. This approach allows for the concentration and collection of microbes, possessing genes encoding specific enzymes or small molecule pathways, from complex or dilute microbial populations in aqueous or terrestrial environments. The basis for the attraction and subsequent enrichment is that microbes possess specific receptors that signal chemotactic attraction towards specific substrates. By binding the substrate to a surface and subsequently incubating the substrate-surface conjugate in the presence of a mixed microbial population, specific members of that population can be collected.

It is an object of the present invention to provide a means for selectively enriching for specific microorganisms from the surrounding environmental matrix. In accomplishing these and other objects, there has been provided, in accordance with one aspect of the present invention, a device for collecting a population of microorganisms from an environmental sample comprising a solid support having a surface for attaching a selectable microbial enrichment media.

In one aspect of the invention, microbial enrichment media containing a microbial attractant is used to selectively lure members of the environmental community to the device. In another aspect of the invention, bioactive compounds which inhibit the growth of unwanted organisms is included in the microbial enrichment media to further enhance selection of desirable microorganisms.

In yet another aspect of the invention, a method for isolating microorganisms from an environmental sample comprising contacting the sample with a device having a solid support and a surface for attaching a selectable microbial enrichment media and isolating the population from the device is provided.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The present invention provides a device for the isolation and containment of microorganisms and a method for acquiring in situ enrichments of uncultivated microorganisms. The enrichment process can increase the likelihood of recovering rare species and previously uncultivated members of a microbial population.

In situ enrichment can be achieved in the present invention by using a microbial containment device consisting of growth substrates and nutritional amendments with the intent to selectively lure members of the surrounding environmental matrix. Choice of substrates (carbon sources) and nutritional amendments (i.e., nitrogen, phosphorous, etc.) is dependent upon the members of the community for which one desires to enrich. The exact composition depends upon which members of the community one desires to enrich and which members of the community one desires to inhibit. These containment devices are then deployed in desired biotopes for a period of time to allow attraction and growth of desirable microbes.

Substrates of the invention can include monomers and polymers. Monomers of substrates, such as glucosamine, cellulose, pentanoic or other acids, xylan, chitin, etc., can be utilized for attraction of certain types of microbes. Using monomers allows one to depend on attraction for the collecting, versus the presence of substrate receptors on cells. This could provide the added benefit of allowing one to acquire more biodiversity. Polymers can also be used to attract microbes that can degrade them.

Specific microbes of interest can be captured and concentrated from dilute populations in aqueous environments thereby obviating the need to concentrate microorganisms from large volumes of water. These devices can also be implanted in soil environments to enrich microbes from terrestrial habitats. Substrates such as cellulose or chitin can be attached to the surface material to attract specific classes of microbes, such as the actinomyces, which are a rich source of secondary metabolites.

Figure 1:
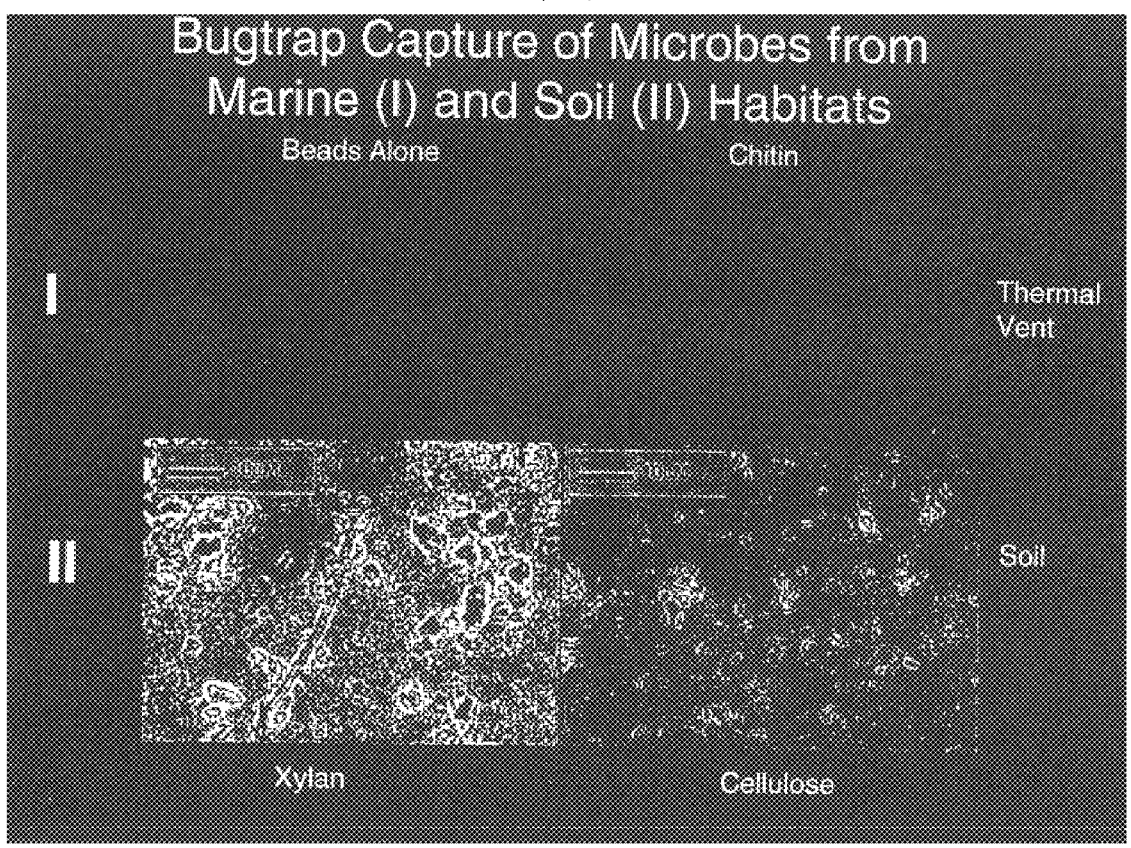
FIG. 1 illustrates the substrate spectrum fingerprints and optimum reaction temperatures of five of novel esterases showing the diversity in these enzymes. EST# indicates the different enzyme; the temperatures indicate the optimal growth temperatures for the organisms from which the esterases were isolated; "E" indicates the relative activity of each esterase enzyme on each of the given substrates indicated (Hepanoate being the reference).
Figure 2:
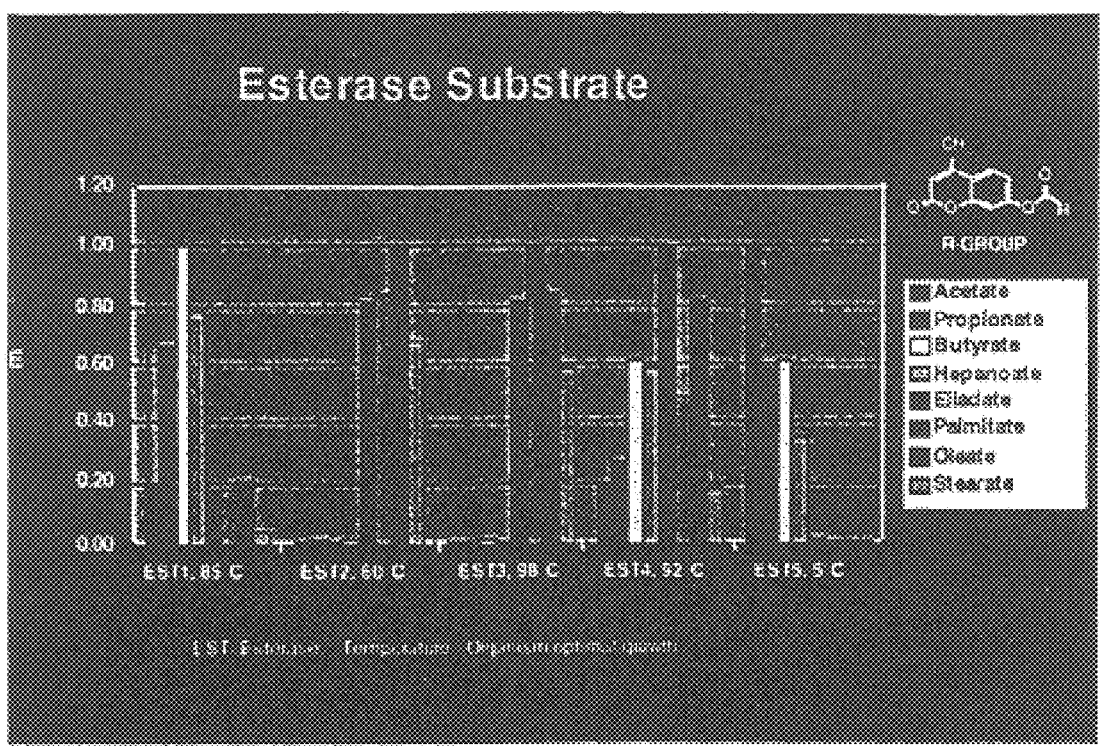
FIG. 2 illustrates the capture of microbes from marine and soil habitats as detailed in the present invention. These photos demonstrate the difference in the types of microbes collected from a soil environment when utilizing two different types of substrates (cellulose and xylan). These photos also demonstrate the difference in employing beads alone versus beads with substrate attached (chitin).

Utilizing the present invention, in situ enrichment can be readily achieved. FIG. 2 demonstrates the capture of microbes from different habitats, as detailed in the present invention. These photos demonstrate the difference in the types of microbes collected from a soil environment when utilizing two different types of substrates (cellulose and xylan). These photos also demonstrate the difference in employing beads alone versus beads with substrate attached (chitin).

In a preferred embodiment, the invention relates to a microbial containment device for collecting a population of microorganisms from an environmental sample comprising a solid support having a surface for attaching a selectable microbial enrichment media.

In another preferred embodiment of the invention, a method for isolating microorganisms from an environmental sample comprising contacting the sample with a device having a solid support and a surface for attaching a selectable microbial enrichment media and isolating the population from the device is provided.

"Selective microbial enrichment media", as used herein, is any medium containing elements which enhance the growth of certain organisms and/or inhibit the growth of other organisms present in the surrounding environment. The media of the present invention is useful when the organism targeted for enrichment is present in relatively small numbers compared to other organisms growing in the surrounding matrix. For example, a selective microbial enrichment media containing the antibiotics colistin and nalidixic acid will inhibit the growth of gram-negative bacteria but not the growth of gram-positives. The selectivity of the microbial enrichment media can be further enhanced by the addition of a specific substrate such as, for example, cellulose, to the colistin and nalidixic acid containing media. Therefore, a microbial containment device incorporating the aforementioned microbial enrichment media will be selective for gram-positive organisms which are capable of utilizing cellulose as an energy source.

The term "solid support", as used herein, is any structure which provides a supporting surface for the attachment of a selectable microbial enrichment media. Well known solid supports that may be used for screening assays of the invention include, but are not restricted to, glass beads, silica aerogels, agarose, Sepharose, Sephadex, nitrocellulose, polyethylene, dextran, nylon, natural and modified cellulose, polyacrylamide, polystyrene, polypropylene, and microporous polyvinylidene difluoride membrane. It is understood that any material which allows for the attachment and support of a selectable media is included in the present invention. By using large surface area materials, such as, for example, glass beads or silica aerogels, a high concentration of microbes can be collected in a relatively small device holding multiple collections of substrate-surface conjugates.

In one aspect of the invention, substrates are conjugated to solid surfaces prior to deployment into the environment of choice. Such conjugation is preferably a chemical conjugation. Large surface area materials, such as glass beads or silica aerogels are preferably utilized as surfaces in the present invention. It is anticipated that there are a variety of surface area materials that could be utilized effectively in the present invention. Conjugation or immobilization of substrates to the surface material may occur via a variety of methods apparent to the skilled artisan. One example of derivitization of glass beads is described in an Example provided below. It is anticipated that any of a variety of conjugation or immobilization strategies can be employed to immobilize substrates to surfaces in the present invention.

Derivitized surface area materials, such as glass beads or silica aerogels, of the present invention are contained in separate device(s) before placement into the environment of interest. Preferably, such containment devices are of the type which allow migration of microbes in while simultaneously containing the derivitized materials. For example, particularly preferred containers are mesh filters, such as those available from Spectrum in Houston, Tex., which have been manipulated to contain the derivitized materials. For example, filters can be cut into squares, derivitized materials can be placed in the center, the filter can be folded in half and the three sides can be glued shut to create a containment device. Mesh filters, or the like, can then be placed in any device to be used as a solid support which will contain the mesh filter for deployment into the environment. Particularly preferred devices are made of inert materials, such as plexiglass.

Alternatively, any device which allows migration of microbes while simultaneously containing the materials can be employed with the present invention. For example, Falcon tubes (VWR, Fisher Scientific) or the like may be employed to contain the derivitized materials directly. Said tubes can be punctured utilizing a sharp instrument to yield a device which allows microbe migration into or out of the device.

The anchored component of the selectable enrichment medium can be immobilized by non-covalent or covalent attachments. Non-covalent attachment can be accomplished by coating a solid surface with a solution of, for example, a protein which is specifically recognized by a receptor displayed on the cell membrane of a target organism. Alternatively, an immobilized antibody, preferably a monoclonal antibody, specific for the protein to be immobilized can be used to anchor the protein to the solid surface. The surfaces can be prepared in advance and stored.

In another aspect, the present invention relates to a method of selective in situ enrichment of bacterial and archaeal microorganisms utilizing a microbial attractant attached to a solid surface. A "microbial attractant", as used herein, is defined as any composition which selectively precipitates or induces the migration of microorganisms to a device containing a microbial enrichment media. A microbial attractant is further defined as any composition which selectively augments the survival of a microorganism which contacts a microbial enrichment media contained in a device of the present invention. For example, microorganisms routinely display chemotactic responses to environmental stimuli perceived as energy sources, such as a carbon source.

Any particular carbon source can be utilized by some members of the community and not others. Carbon source selection thus depends upon the members of the community one desires to enrich. For example, members of the Streptomycetales tend to utilize complex, polymeric substrates such as cellulose, chitin, and lignin. These complex subtrates, while utilized by other genera, are recalcitrant to most bacteria.

In another aspect, the use of additional nitrogen sources may be called for depending upon the choice for carbon source. For example, while chitin is balanced in its C:N ratio, cellulose is not. To enhance utilization of cellulose (or other carbon-rich substrates), it is often useful to add nitrogen sources such as nitrate or ammonia. Further, the addition of trace elements may enhance growth of some members of a community while inhibiting others.

In another aspect of the invention, compounds useful as growth inhibitors of eukaryotic organisms can be included in the device of the present invention. Growth inhibitors of eukaryotic organisms include any compound which selectively prevents the growth of eukaryotic organisms. Such inhibitors can include, for example, one or more commercially available compounds such as nystatin, cycloheximide, and/or pimaricin or other antifungal compounds. These compounds may be sprinkled as a powder or incorporated as a liquid in the selectable microbial enrichment medium. It is anticipated that other selective agents can be employed to inhibit the growth of undesired species or promote the growth of desired species. For example, obtaining bacterial and archaeal species can be complicated by the presence of eukaryotic organisms which can out-compete desired bacterial species for the available substrate. Therefore, including selective agents, such as antifungal agents or other eukaryotic growth inhibitors, in the device of the present invention promotes the growth of target microorganisms.

In yet another aspect, compounds which inhibit the growth of some bacterial species, but not others, may be incorporated into the enrichment medium. Growth inhibitors for prokaryotic organisms include any compound which prevents the proliferation of prokaryotic cells. Such compounds include, but are not limited to, polymyxin, penicillin, and rifampin. Use of the compounds is dependent upon which members of the bacterial community one desires to enrich. For example, while a majority of the Streptomyces are sensitive to polymyxin, penicillin, and rifampin, these may be used to enrich for "rare" members of the family which are resistant. Selective agents may also be used in enrichments for archaeal members of the community.

In the context of the present invention, a containment device containing a microbial enrichment medium can incorporate, for example, a complex carbon source as an attractant, nystatin as an inhibitor of eukaryotic organisms and rifampin as an inhibitor of selected prokaryotic organisms. It is understood that attractants, eukaryotic inhibitors and prokaryotic inhibitors can be used individually, or in any combination, as a component of a selectable microbial enrichment medium of the present invention. It is further understood that a device of the present invention can include any appropriate solid support in combination with any microbial enrichment medium suitable for an environmental matrix or for the isolation of microorganisms of interest. An environmental matrix can include a marine environment, a terrestrial environment or a combination of marine and terrestrial environment. Moreover, an environmental matrix can include those organisms which exist in surroundings which are neither solid nor liquid, such as those organisms which remain airborne. The device of the present invention can be used to filter such organisms from the atmosphere or any other gaseous environment. It is further envisioned that a containment device of the present invention can be used for the isolation of microorganisms from non-terrestrial environments, such as those existing on planets other than earth. For example, a containment device containing a microbial enrichment medium designed to attract microorganisms which can exist on the planet Mars is included in the present invention. Such a device would incorporate features designed to attract microorganisms capable of existing in an environmental matrix not substantially different from those which are currently encountered on earth. Further, a sufficient amount of data concerning environmental conditions on planets other than earth is available such that a containment device of the present invention can be designed to incorporate elements specific to those environments.

In another aspect, the present invention can be employed to isolate and identify microorganisms useful in bioremediation. Bioremediation is a process which utilizes microorganisms to remove or detoxify toxic or unwanted chemicals from an environment. The device of the present invention can be modified to contain a medium which selectively enriches for those organisms capable of attaching to, or detoxifying, toxic or unwanted chemicals. For example, halogenated organic compounds have had widespread use as fungicides, herbicides, insecticides, algaecides, plasticizers, solvents, hydraulic fluids, refrigerants and intermediates for chemical syntheses. As a result, they constitute one of the largest groups of environmental pollutants. Chloroorganic compounds comprise the largest fraction of these materials, having been synthesized by large scale processes over the past few decades. Their ubiquitous use and distribution in our ecosystem has raised concern over their possible effects on public health and the environment. Therefore, a need exists for the identification of microorganisms which are capable of removing these, and other, chemicals from the environment. The inclusion, for example, of chlorinated organic compounds in a selectable enrichment medium of the present invention can aid the isolation of organisms attracted to such a compound. Once identified, the organism can be used as a natural and inexpensive means of detoxifying environments known to contain such pollutants.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Surface Derivitization—N-Acetyl B-D-glucosamine-phenylisothiocyanate (Activated Substrate) onto Glass Beads Glass beads can be derivitized with N-Acetyl B-D-glucosamine-phenylisothiocyanate as follows:

Bead Preparation:

1. Mix:
   30 ml glass beads (Biospec Products, Bartlesville, Okla.)
   50 ml APS/Toluene (10%) (APS—Aminopropyltriethoxysilane) (Aldrich)
2. Reflux overnight 3. Decant and wash 3 times with Toluene
4. Wash 3 times with ethanol and dry in oven Derivitize with N-Acetyl B-D-glucosamine-phenylisothiocyanate as follows:

5. Combine in Falcon Tube:
   25 ml prepared glass beads from above
   15 ml 0.1M $NaHCO_3$ + 25 mg N-Acetyl-B-D-glucosamine-PITC (Sigma Chemical Co.) +1 ml DMSO
6. Add 10 ml $NaHCO_3$ +1 ml DMSO.
7. Pour over glass beads.
8. Let shake in Falcon Tube overnight.
9. Wash with 20 ml 0.1M $NaHCO_3$.
10. Wash with 50 ml ddH2O.
11. Dry at 55° C. for 1 hour.

EXAMPLE 2

Surface Derivitization—Birchwood Xylane (Polymer) onto Sol Gel

Glass Mixture (slurry):
1. Combine on ice:
   75 ml TMOS (Tetramethylorthosilicate—"Sol Gel") (Aldrich)
   30 ml H2O
   Slowly add 2 ml of 0.05M HCl
   Slowly add while stiring 2 ml of 0.05M NaOH to increase pH
2. On stir block in container add:
   10 g of birchwood xylane (Fluka)
   200 ml of 10 mM phosphate buffer, pH 6.0
3. Mix in 105 ml of glass mixture from above. Stir slowly to solid (4–5 minutes).
4. Incubate @55° C. overnight.

The same protocol can be used to derivitize beads with commercially available chitin or cellulose.

EXAMPLE 3

Surface Derivitization—Xylane Monomer onto Glass Beads

1. Mix:
   15 ml 0.1M $NaHCO_3$
   25 mg B-d-xylopyranosylphenylisothiocyanate (Sigma Chemical)
2. Pour over 25 mls prepared beads from Example 1 above.
3. Add 10 ml 0.1M $NaHCO_3$
4. Let sit overnight.

EXAMPLE 4

Microbial Containment Devices with Antibiotics

1. Cut both ends off a 15 ml Falcon Tube (VWR).
2. Cut Spectra/Mesh Nylon Filters (Spectrum, Houston, Tex.) (mesh opening: 70 $\mu$m; % open area: 43; thickness: 70 $\mu$m) into 2 circles of approximately 2.5 cm in diameter.
3. Cover one end of the Falcon Tube with the mesh and attach using Goop, Household Adhesive & Sealant.
4. Make up and filter sterilize the following Dilute Basal Medium:

| | |
|---|---|
| $K_2HPO_4$ | 1.74 g |
| $NaH_2PO_4$ | 1.38 g |
| $(NH_4)_2SO_4$ | 0.5 g |
| $NgSO_4.7H_2O$ | 0.2 g |
| $CaCl_2.2H_2O$ | 0.025 g |
| $KNO_3$ | 0.5 g |
| water | 1 liter |
| cellobiose | 0.001% |

5. Moisten 1 sterile gauze pad (North 3"×3", Fisher) with 10 ml of Dilute Basal Medium (make moist, not dripping wet). This is best handled by laying gauze on a sheet of parafilm, adding medium drop-wise.
6. Allow medium to soak through gauze.
7. Sprinkle approximately 0.5 g of cycloheximide powder on pad and spread around using a spatula.
8. Sprinkle approximately 0.5 g Nystatin (yellow) on the same pad in the same manner.
9. Using tweezers, jam treated gauze pad into Falcon tube.
10. Seal other end of tube with other circle as done previously.
11. Allow to dry (approximately 2 hours).
12. Deploy as desired.

EXAMPLE 5

Sample Collection Using a Microbial Containment Device

The following example describes a type of microbial containment device which can be generated according to the present invention to attract organisms. The following protocol details one method for generating a simple microbial containment device:

1. Puncture small holes using a heated needle or other pointed device into a 15 ml Falcon Tube (VWR, Fisher Scientific).
2. Place approximately 1–5 mls of the derivitized beads from Examples 1, 2 or 3 into a Spectra/mesh nylon filter, such as those available from Spectrum (Houston, Tex.) with a mesh opening of 70 $\mu$m, an open area of 43%, and a thickness of 70 $\mu$m. Seal the nylon filter to create a "bag" containing the beads, using, for instance, Goop, Household Adhesive & Sealant.
3. Place the filter containing the beads into the ventilated Falcon Tube and deploy the tube into the desired biotope for a period of time (typically days).
4. Recover the microbial containment device and associated organisms.

The invention now being fully described, it will be apparent to one of ordinary skill in the art that many changes and modifications can be made thereto without departing from the spirit or scope of the appended claims.

TABLE 1

| Habitat | Cultured (%) |
|---|---|
| Seawater | 0.001–0.1 |
| Freshwater | 0.25 |
| Mesotrophic lake | 0.01–1.0 |
| Unpolluted esturine waters | 0.1–3.0 |
| Activated sludge | 1.0–15.0 |

TABLE 1-continued

| Habitat | Cultured (%) |
| --- | --- |
| Sediments | 0.25 |
| Soil | 0.3 |

What is claimed is:

1. A method for selectively enriching for one or more populations of microorganisms from an in situ environment comprising:
   a) providing a device comprising a container having a plurality of solid support particles contained within the container, a selective microbial enrichment media chemically attached to the solid support particles and a plurality of microorganism permeable openings for entry of microorganisms into said container to contact said enrichment media;
   b) placing device according to a) into an in situ environment causing selective enrichment of the one or more populations of microorganisms from the in situ environment by migration of said one or more populations into the device through said openings; and
   c) removing the enriched one or more populations from the device.

2. The method of claim 1, wherein the selective microbial enrichment media comprises a microbial attractant.

3. The method of claim 2, wherein the microbial attractant is selected from the group consisting of glucosamine, cellulose, pentanoic acid, xylan, lignin, chitin, alkanes, aromatics, chloroorganics, sulphonyls and heavy metals.

4. The method of claim 1, wherein the selective microbial enrichment media comprises a growth inhibitor for eukaryotic organisms.

5. The method of claim 4, wherein the growth inhibitor specific for eukaryotic organisms is selected from the group consisting of nystatin, cycloheximide and pimaricin.

6. The method of claim 1, wherein the selective microbial enrichment media comprises a growth inhibitor for prokaryotic organisms.

7. The method of claim 6, wherein the growth inhibitor specific for prokaryotic organisms is selected from the group consisting of polymyxin, penicillin and rifampin.

8. The method of claim 1, wherein the solid support particles are formed from a material selected from the group consisting of glass, silica aerogels, agarose, Sepharose, Sephadex, nitrocellulose, polyethylene, dextran, nylon, natural and modified cellulose, polyacrylamide, polystyrene, polypropylene, and polyvinylidene difluoride.

9. The method of claim 1, wherein the microorganisms comprise a mixture of terrestrial microorganisms, a mixture of marine microorganisms, or a mixture of terrestrial microorganisms and marine microorganisms.

10. The method of claim 1, wherein the one or more populations of microorganisms are extremophiles.

11. The method of claim 10, wherein the extremophiles are selected from the group consisting of thermophiles, hyperthermophiles, psychrophiles, halophiles, acidophiles, barophiles and psychrotrophs.

12. The method of claim 1, wherein the solid support particles comprise a porous material.

13. The method of claim 1, wherein the solid support particles comprise glass, silica aerogel, or a combination thereof.

14. The method of claim 11, wherein the porous material is a filter material.

15. The method of claim 1, wherein the container is transparent.

16. The method of claim 1, wherein the solid support particles comprise glass beads.

* * * * *